United States Patent
Gharda et al.

(10) Patent No.: US 12,195,421 B2
(45) Date of Patent: Jan. 14, 2025

(54) PROCESS FOR PREPARATION OF TRIFLUOROMETHANESULFINYL CHLORIDE

(71) Applicant: Gharda Chemicals Limited, Maharashtra (IN)

(72) Inventors: Keki Hormusji Gharda, Maharashtra (IN); Diwakar Shenoy, Maharashtra (IN); Laxminarayan Shet, Maharashtra (IN); Sachin Bhiku Jadhav, Maharashtra (IN); Sandip Kedare, Maharashtra (IN)

(73) Assignee: GHARDA CHEMICALS LIMITED, Ratnagiri Maharashtra (IN)

( * ) Notice: Subject to any disclaimer, the term of this patent is extended or adjusted under 35 U.S.C. 154(b) by 560 days.

(21) Appl. No.: 17/439,659

(22) PCT Filed: Mar. 4, 2020

(86) PCT No.: PCT/IB2020/051817
§ 371 (c)(1),
(2) Date: Sep. 15, 2021

(87) PCT Pub. No.: WO2020/188387
PCT Pub. Date: Sep. 24, 2020

(65) Prior Publication Data
US 2022/0153692 A1    May 19, 2022

(30) Foreign Application Priority Data
Mar. 16, 2019 (IN) .............................. 201921010323

(51) Int. Cl.
*C07C 313/02* (2006.01)
*C07C 315/02* (2006.01)

(52) U.S. Cl.
CPC .......... *C07C 313/02* (2013.01); *C07C 315/02* (2013.01)

(58) Field of Classification Search
CPC .............................. C07C 313/02; C07C 315/02
See application file for complete search history.

(56) References Cited

U.S. PATENT DOCUMENTS

| | | | | |
|---|---|---|---|---|
| 2,347,151 A * | 4/1944 | Crawford | ................ | C01B 11/04 423/473 |
| 3,274,181 A * | 9/1966 | Foote | ................... | C07D 493/08 560/231 |
| 5,068,408 A * | 11/1991 | Raynor | ................... | C07B 41/08 568/426 |
| 2012/0103138 A1* | 5/2012 | Welham | ................... | C22B 3/10 75/743 |

FOREIGN PATENT DOCUMENTS

IN     201621000857 A    10/2017
WO     201035776 A1    4/2010

OTHER PUBLICATIONS

Int'l Search Report issued Jun. 23, 2020 in Int'l Application No. PCT/IB2020/051817.

* cited by examiner

*Primary Examiner* — Rosalynd A Keys
(74) *Attorney, Agent, or Firm* — Panitch Schwarze Belisario & Nadel LLP

(57) ABSTRACT

A process for the preparation of trifluoromethanesulfinyl chloride is provided. Trifluoromethanesulfinyl chloride is used as an intermediate for preparing pesticides and insecticides. Trifluoromethanesulfinyl chloride is represented by Formula I:

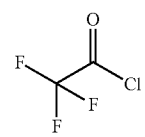

Trifluoromethanesulfinyl chloride (I)

The process for the preparation of trifluoromethanesulfinyl chloride employs readily available reagents and does not involve formation of toxic by-products, and is thus a simple, economic, and environmental-friendly process for the preparation of trifluoromethanesulfinyl chloride.

13 Claims, No Drawings

PROCESS FOR PREPARATION OF TRIFLUOROMETHANESULFINYL CHLORIDE

CROSS-REFERENCE TO RELATED APPLICATIONS

This application is a Section 371 of International Application No. PCT/IB2020/051817, filed Mar. 4, 2020, which was published in the English language on Sep. 24, 2020, under International Publication No. WO 2020/188387 A1, which claims priority under 35 U.S.C. § 119 (b) to Indian application No. 201921010323, filed Mar. 16, 2019, the disclosure of each of which is incorporated herein by reference in their entireties.

FIELD

The present disclosure relates to a process for the preparation of trifluoromethanesulfinyl chloride.

BACKGROUND

The background information herein below relates to the present disclosure but is not necessarily prior art.

Trifluoromethanesulfinyl chloride is used as an intermediate for the preparation of commercially important compounds. The purity of the trifluoromethanesulfinyl chloride directly affects the quality of the synthesized compound. Thus, it is important to synthesize trifluoromethanesulfinyl chloride with high purity.

A known process for the preparation of trifluoromethanesulfinyl chloride involves chlorination of trifluoromethanesulfinic acid. Another process for its preparation involves chlorination of sodium trifluoromethanesulfonate. Trifluoromethanesulfinyl chloride can also be prepared by oxidation of trifluoromethanesulfenyl chloride. These processes are associated with the drawbacks such as unwanted oxidation of trifluoromethylsulfoxide to the corresponding sulfone, use of costly raw material, and low yield.

There is, therefore, felt a need for a simple and an economical process for the preparation of trifluoromethanesulfinyl chloride with high yield and high purity.

Objects

Some of the objects of the present disclosure, which at least one embodiment herein satisfies, are as follows:

An object of the present disclosure is to ameliorate one or more problems of the prior art or to at least provide a useful alternative.

Another object of the present disclosure is to provide a process for the preparation of trifluoromethanesulfinyl chloride with high yield and high purity.

Yet another object of the present disclosure is to provide a simple, economic, and environmental-friendly process for the preparation of trifluoromethanesulfinyl chloride.

Other objects and advantages of the present disclosure will be more apparent from the following description, which is not intended to limit the scope of the present disclosure.

SUMMARY

The present disclosure relates to a process for the preparation of trifluoromethanesulfinyl chloride. The process comprises mixing ortho-chlorobenzyltrifluoromethylsulfide with at least one fluid medium and water to obtain a first mixture. Chlorine gas is passed through the first mixture under the continuous stirring at a first predetermined temperature to obtain a resultant mixture. The resultant mixture is allowed to stand in order to separate an organic phase and an aqueous phase. The organic phase is separated from the aqueous phase to obtain separated organic phase. The separated organic phase is concentrated to obtain a second mixture comprising ortho-chlorobenzyltrifluoromethylsulfoxide. Further, chlorine is passed through the second mixture under continuous stirring in the presence of at least one activator at a second predetermined temperature to obtain a product mixture comprising trifluoromethanesulfinyl chloride and ortho-chlorobenzyl chloride. The product mixture is fractionally distilled to obtain a first fraction comprising trifluoromethanesulfinyl chloride and a second fraction comprising ortho-chlorobenzyl chloride. The first predetermined temperature and the second predetermined temperature is in the range of 10° C. to 30° C. The chlorine gas is passed in the second mixture until the second mixture reaches a third predetermined temperature. The third predetermined temperature is in the range of 10° C. to 90° C. Trifluoromethanesulfinyl chloride obtained by the process of the present disclosure has purity in the range of 95% to 99.9%.

DETAILED DESCRIPTION

Embodiments are provided so as to thoroughly and fully convey the scope of the present disclosure to the person skilled in the art. Numerous details are set forth, relating to specific components, and methods, to provide a complete understanding of embodiments of the present disclosure. It will be apparent to the person skilled in the art that the details provided in the embodiments should not be construed to limit the scope of the present disclosure. In some embodiments, well-known processes, well-known apparatus structures, and well-known techniques are not described in detail.

The terminology used, in the present disclosure, is only for the purpose of explaining a particular embodiment and such terminology shall not be considered to limit the scope of the present disclosure. As used in the present disclosure, the forms "a," "an," and "the" may be intended to include the plural forms as well, unless the context clearly suggests otherwise. The terms "comprises," "comprising," "including," and "having," are open ended transitional phrases and therefore specify the presence of stated features, integers, steps, operations, elements, modules, units and/or components, but do not forbid the presence or addition of one or more other features, integers, steps, operations, elements, components, and/or groups thereof. The particular order of steps disclosed in the method and process of the present disclosure is not to be construed as necessarily requiring their performance as described or illustrated. It is also to be understood that additional or alternative steps may be employed.

The terms first, second, third, etc., should not be construed to limit the scope of the present disclosure as the aforementioned terms may be only used to distinguish one element, component, region, layer or section from another component, region, layer or section. Terms such as first, second, third etc., when used herein do not imply a specific sequence or order unless clearly suggested by the present disclosure.

Trifluoromethanesulfinyl chloride is used as an intermediate for the preparation of commercially important compounds. The purity of trifluoromethanesulfinyl chloride is important for the synthesis of these compounds, as the purity of trifluoromethanesulfinyl chloride directly affects the quality of the synthesized compounds. The present disclosure envisages a process for the preparation of trifluoromethanesulfinyl chloride with high yield and high purity.

The present disclosure provides a process for the preparation of trifluoromethanesulfinyl chloride (I):

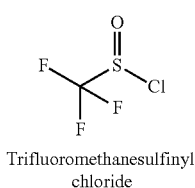

Trifluoromethanesulfinyl chloride

The scheme for the preparation of trifluoromethanesulfinyl chloride (I) from ortho-chlorobenzyltrifluoromethylsulfide (II), in accordance with the process of the present disclosure, is shown in Scheme I:

Scheme 1: Process for the preparation of trifluoromethanesulfinyl chloride (I)

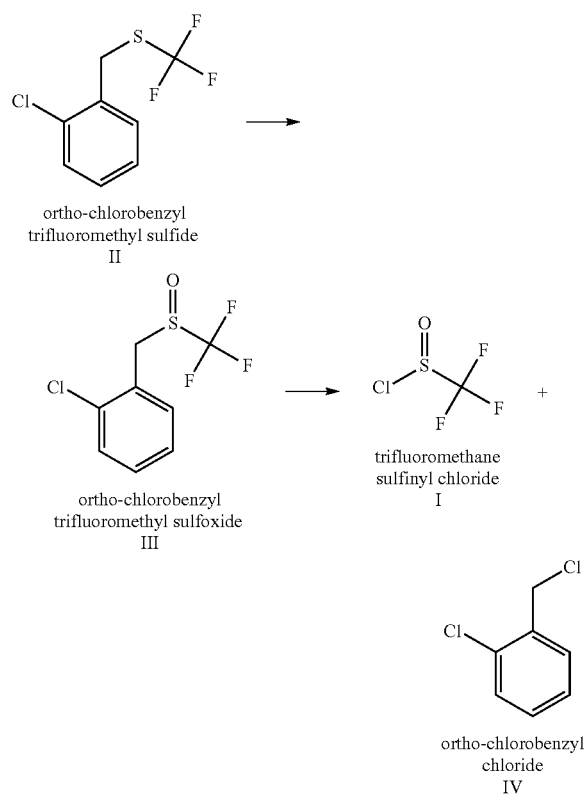

The preparation of trifluoromethanesulfinyl chloride, in accordance with the process of the present disclosure is described in detail herein below:

Ortho-chlorobenzyltrifluoromethylsulfide is mixed with an aqueous fluid medium to obtain a first mixture. Chlorine gas is passed in the first mixture at a first predetermined temperature to obtain a resultant mixture. The so obtained resultant mixture is allowed to stand in order to separate an aqueous phase and an organic phase.

In accordance with the embodiments of the present disclosure, the mole ratio of ortho-chlorobenzyltrifluoromethylsulfide to chlorine gas in the step of passing chlorine gas in the first mixture is in the range of 1:1 to 1:1.5. In an exemplary embodiment of the present disclosure, the mole ratio of ortho-chlorobenzyltrifluoromethylsulfide to chlorine gas is 1:1.

In accordance with the embodiments of the present disclosure, the fluid medium is at least one selected from the group consisting of dichloromethane, dichloroethane, monocholoro-benzene, chloroform, bromobenzene, carbon tetrachloride.

In accordance with the present disclosure, the ratio of the amount of the fluid medium and the amount of water can be 1:1.

The first predetermined temperature can be in the range of 10° C. to 30° C. Although, passing of chlorine gas starts at 10° C., since the chlorination reaction (passing of chlorine gas in the first mixture) is exothermic, the first resultant mixture reaches the temperature to 30° C. while the chlorine gas is being continuously passed.

Typically, the first predetermined temperature is 15° C. to 20° C. In an embodiment, the chlorine gas is passed at 15° C. and is passed continuously till the first resultant mixture reaches the temperature to 20° C.

In this process step, chlorine gas reacts with water from aqueous fluid medium to form hypochlorous acid (HOCl) in situ. Hypochlorous acid (HOCl) is a mild acid and mild oxidizing agent that facilitates the selective oxidation of sulfide to sulfoxide. In accordance with the present disclosure, addition of chlorine in aqueous fluid medium is an exothermic reaction and hence does not require further heating. The reaction can be carried out at mild reaction conditions.

The organic phase is separated from the aqueous phase to obtain a separated organic phase. In accordance with the present disclosure, the separated organic phase is washed with sodium bicarbonate solution to remove mineral acidity. In an embodiment of the present disclosure, the step of washing separated organic phase involves washing the separated organic layer with aqueous solution of sodium bi-carbonate and/or sodium bi-sulfide.

In another embodiment of the present disclosure, the step of washing separated organic phase involves sequentially washing the separated organic layer with aqueous sodium bi-carbonate solution and an aqueous sodium bi-sulfide solution.

Washing with aqueous sodium bi-carbonate solution is carried out to remove residual acid impurities; and washing with aqueous sodium bi-sulfide solution is carried out to remove residual hypochlorous acid/Cl$_2$ from the organic phase.

In accordance with the embodiments of the present disclosure, the strength of the aqueous sodium bi-carbonate solution is in the range of 1.0% to 5.0% W/V.

In accordance with the embodiments of the present disclosure, the strength of the aqueous sodium bi-sulfide solution is in the range of 5% to 30%.

The separated organic phase is concentrated to obtain a second mixture comprising ortho-chlorobenzyltrifluoromethylsulfoxide. In an embodiment, the separated organic phase is concentrated at a temperature in the range of 40° C. to 90° C. at ambient pressure or at reduced pressure. Typically, the separated organic phase is concentrated at a temperature in the range of 70° C. to 80° C. at ambient pressure or at reduced pressure.

Water is removed from the washed organic phase by azeotropic distillation till the water content is less than 0.5% to obtain a second mixture comprising ortho-chlorobenzyltrifluoromethylsulfoxide.

It is observed that keeping the water content of the second mixture below 0.5% provides higher yield of trifluoromethanesulfinyl chloride.

Chlorine gas is passed in the second mixture under continuous stirring and in the presence of at least one activator at a second predetermined temperature to obtain a product mixture comprising trifluoromethanesulfinyl chloride and ortho-chlorobenzyl chloride.

In accordance with the embodiments of the present disclosure, the mole ratio of ortho-chlorobenzyltrifluoromethylsulfoxide to chlorine gas in the step of passing chlorine gas in the second mixture is in the range of 1:1 to 1:1.5. In an exemplary embodiment of the present disclosure, the mole ratio of ortho-chlorobenzyltrifluoromethylsulfoxide to chlorine gas is 1:1.

The second predetermined temperature can be in the range of 10° C. to 30° C. Typically, the second predetermined temperature is 10° C. to 20° C.

The chlorine gas is passed in the second mixture until the second mixture reaches a third predetermined temperature. The third predetermined temperatures can be in the range of 10° C. to 90° C.

In accordance with the embodiments of the present disclosure, the activator is selected from the group consisting of iodine, di-tert-butyl peroxide, benzoyl peroxide, and azobisisobutyronitrile. In an exemplary embodiment of the present disclosure, the activator is iodine.

In accordance with the embodiments of the present disclosure, the mole ratio of ortho-chlorobenzyltrifluoromethylsulfoxide to the activator is in the range of 1:0.001 to 1:0.01. In an exemplary embodiment of the present disclosure, the mole ratio of ortho-chlorobenzyltrifluoromethylsulfoxide to the activator is 1:0.007.

The product mixture is fractionally distilled to obtain a first fraction comprising trifluoromethanesulfinyl chloride and a second fraction comprising ortho-chlorobenzyl chloride.

Trifluoromethanesulfinyl chloride obtained has purity in the range of 95% to 99.9%.

In accordance with the embodiments of the present disclosure, the stirring of the first reaction mixture is carried out for a time period in the range of 1 hour to 5 hours; the stirring of the second reaction mixture is carried out for a time period in the range of 1 hour to 5 hours.

The present disclosure provides the process for the preparation of trifluoromethanesulfinyl chloride with a yield in the range of 85% to 95%.

The process of the present disclosure provides trifluoromethanesulfinyl chloride with more than 95% GLC purity. Therefore, trifluoromethanesulfinyl chloride obtained by the process of the present disclosure can be directly used for the synthesis of commercially important compounds.

The process of the present disclosure is simple. The process employs cheap and readily available reagents. Further, the fluid medium used is charged only once; subsequent steps are carried out in the same fluid medium. Ortho-chlorobenzyl chloride recovered from the product mixture can be re-used as a raw material for synthesis of Compound of Formula II. Thus, the process of the present disclosure is economical. Furthermore, the process of the present disclosure does not involve formation of toxic by-product. Therefore, the process of the present disclosure is environmental friendly.

The foregoing description of the embodiments has been provided for purposes of illustration and not intended to limit the scope of the present disclosure. Individual components of a particular embodiment are generally not limited to that particular embodiment, but, are interchangeable. Such variations are not to be regarded as a departure from the present disclosure, and all such modifications are considered to be within the scope of the present disclosure.

The present disclosure is further described in light of the following experiments which are set forth for illustration purpose only and not to be construed for limiting the scope of the disclosure. The following experiments can be scaled up to industrial/commercial scale and the results obtained can be extrapolated to industrial scale.

EXPERIMENTAL DETAILS

Experiment-I: Preparation of Trifluoromethanesulfinyl Chloride (I) in Accordance with the Present Disclosure Ortho-chloro benzyl trifluoro methyl sulfide (II) (226.5 gm), monochlorobenzene (50 ml) and $H_2O$ (400 ml) were charged in 1-lit vertical reactor to obtain a first mixture. Chlorine gas (74.55 gm) was then passed through the first mixture at 15° C. Since the reaction is exothermic, the first mixture reaches to 25° C. while the chlorine is being passed over a period of 3 hrs to obtain a first resultant mixture.

The so obtained first resultant mixture was then allowed to settle and separated into organic layer comprising ortho-chloro benzyl trifluoro methyl sulfoxide (III) and aqueous layer comprising hydrochloric acid.

Organic layer comprising ortho-chloro benzyl trifluoro methyl sulphoxide was then dehydrated by azeotropic distillation 60-65° C. under reduced pressure till the water content of the organic layer is less than 0.5% to obtain a second mixture.

In so obtained second mixture comprising dehydrated ortho-chloro benzyl trifluoro methyl sulphoxide and monochlorobenzene, iodine (1 gm) was added. Chlorine gas (71.0 gm) was then passed at 20° C. Since the reaction is exothermic, the first mixture reaches to 30° C. while the chlorine is being passed over a period of 2 hrs to obtain a first resultant mixture.

The product mixture comprising ortho-chloro benzyl chloride (IV), monochlorobenzene and trifluoro methane sulfinyl chloride (I) was distilled up to 95° C. liquid & vapor temperature of 40° C.-41° C. to collect trifluoro methane sulfinyl chloride (142 gm).

Yield=93.1%; and
Purity=99.0%.

Experiment-II: Preparation of Ortho-Chloro Benzyl Trifluoro Methyl Sulphoxide (III)

Ortho-chloro benzyl trifluoro methyl sulfide (II) (226.5 gm), dichloromethane (50 ml) and $H_2O$ (300 ml) were charged in 1-lit vertical reactor to obtain a first mixture. Chlorine gas (74 gm) was then passed through the first mixture at 20° C. Since the reaction is exothermic, the first mixture reaches to 25° C. while the chlorine is being passed over a period of 5 hrs to obtain a first resultant mixture.

The so obtained first resultant mixture was then allowed to settle and separated into organic layer comprising ortho-chloro benzyl trifluoro methyl sulfoxide (III) and aqueous layer comprising hydrochloric acid.

The organic layer comprising ortho-chloro benzyl trifluoro methyl sulfoxide (III) was then concentrated at 50° C. to obtain ortho-chloro benzyl trifluoro methyl sulfoxide (III) (240 gm) with 95% GLC purity.

Experiment-III: Preparation of Ortho-Chloro Benzyl Trifluoro Methyl Sulphoxide (III)

Ortho-chloro benzyl trifluoro methyl sulfide (II) (226.5 gm), dichloroethane (50 ml) and $H_2O$ (300 ml) were charged in 1-lit vertical reactor to obtain a first mixture. Chlorine gas (74 gm) was then passed through the first mixture at 10° C. Since the reaction is exothermic, the first mixture reaches to 20° C. while the chlorine is being passed over a period of 4 hrs to obtain a first resultant mixture.

The so obtained first resultant mixture was then allowed to settle and separated into organic layer comprising ortho-chloro benzyl trifluoro methyl sulfoxide (III) and aqueous layer comprising hydrochloric acid.

The organic layer comprising ortho-chloro benzyl trifluoro methyl sulfoxide (III) was then concentrated at 60-65° C. under reduced pressure to obtain ortho-chloro benzyl trifluoro methyl sulfoxide (III) (240 gm) with 96% GLC purity.

Experiment-IV: Preparation of Ortho-Chloro Benzyl Trifluoro Methyl Sulphoxide (III)

Ortho-chloro benzyl trifluoro methyl sulfide (II) (226.5 gm), mono-chloro benzene (50 ml) and $H_2O$ (400 ml) were charged in 1-lit vertical reactor to obtain a first mixture. Chlorine gas (74.55 gm) was then passed through the first mixture at 20° C. Since the reaction is exothermic, the first mixture reaches to 25° C. while the chlorine is being passed over a period of 5 hrs to obtain a first resultant mixture.

The so obtained first resultant mixture was then allowed to settle and separated into organic layer comprising ortho-chloro benzyl trifluoro methyl sulfoxide (III) and aqueous layer comprising hydrochloric acid.

The organic layer comprising ortho-chloro benzyl trifluoro methyl sulfoxide (III) was then concentrated at 75-80° C. under reduced pressure to obtain ortho-chloro benzyl trifluoro methyl sulfoxide (III) (240 gm) with 93% GLC purity.

Experiment-V: Preparation of Ortho-Chloro Benzyl Trifluoro Methyl Sulphoxide (III)

Ortho-chloro benzyl trifluoro methyl sulfide (II) (226.5 gm), and $H_2O$ (500 ml) were charged in 1-lit vertical reactor to obtain a first mixture. Chlorine gas (74.55 gm) was then passed through the first mixture at 15° C. Since the reaction is exothermic, the first mixture reaches to 25° C. while the chlorine is being passed over a period of 3 hrs to obtain a first resultant mixture.

The so obtained first resultant mixture was then allowed to settle and separated into organic layer comprising ortho-chloro benzyl trifluoro methyl sulfoxide (III) and aqueous layer comprising hydrochloric acid.

The organic layer comprising ortho-chloro benzyl trifluoro methyl sulfoxide (III) was then concentrated at 65-75° C. under reduced pressure to obtain ortho-chloro benzyl trifluoro methyl sulfoxide (III) (245 gm) with 94% GLC purity.

Purification of Ortho-Chloro Benzyl Trifluoro Methyl Sulphoxide (III)

Ortho-chloro benzyl trifluoro methyl sulphoxide (III) (200 gm) (95% purity and 4.5% ortho-chloro benzyl chloride) and n-hexane (200 ml) were charged in 1-lit vertical reactor, followed by heating at 45-50° C. The resultant mixture was then cooled to 10-12° C. with stirring and equilibrated for 1 hr. The slurry obtained was filtered and dried to remove trap n-hexane to get pure ortho-chloro benzyl trifluoro methyl sulphoxide (III) (152 gm) with purity=99.7%.

Experiment-VI: Preparation of Trifluoromethanesulfinyl Chloride (I)

Ortho-chloro benzyl trifluoro methyl sulphoxide (III) (242.5 gm) and iodine (1 gm) were charged in 1-lit vertical reactor to obtain a mixture. Chlorine gas (71 gm) was then passed through the mixture at 20° C. Since the reaction is exothermic, the first mixture reaches to 30° C. while the chlorine is being passed over a period of 4 hrs to obtain a first resultant mixture.

The product mixture comprising ortho-chloro benzyl chloride (IV), monochlorobenzene and trifluoro methane sulfinyl chloride (I) was distilled up to 85° C. mass temperature and vapor temperature of 40-41° C. to collect trifluoro methane sulfinyl chloride (129.6 gm).

Yield=85%; and
Purity=99.5%.

Experiment-VII: Preparation of Trifluoromethanesulfinyl Chloride (I)

Ortho-chloro benzyl trifluoro methyl sulphoxide (III) (242.5 gm) and dichloro methane (100 mL) were mixed in 1-lit vertical reactor, followed by addition of iodine (1 gm) to obtain a mixture. Chlorine gas (71 gm) was then passed through the mixture at 15° C. Since the reaction is exothermic, the first mixture reaches to 20° C. while the chlorine is being passed over a period of 4 hrs to obtain a product mixture.

The product mixture comprising ortho-chloro benzyl chloride (IV), dichloromethane and trifluoro methane sulfinyl chloride (I) was distilled upto 85° C. mass temperature and vapor temperature of 40-41° C. to collect mixture of dichloromethane+trifluoro methane sulfinyl chloride (268 gm).

Yield=89.6%; and
Purity=51.0%.

Experiment-VIII: Preparation of Trifluoromethanesulfinyl Chloride (I)

Ortho-chloro benzyl trifluoro methyl sulphoxide (III) (242.5 gm) and iodine (1 gm) were charged in 1-lit vertical reactor to obtain a mixture. Chlorine gas (71 gm) was then passed through the mixture at 30° C. Since the reaction is exothermic, the first mixture reaches to 70° C. while the chlorine is being passed with simultaneous collection of trifluoro methane sulfinyl chloride (I) (122 gm).

Yield=80%; and
Purity=99.7%.

Experiment-IX: Preparation of Trifluoromethanesulfinyl Chloride (I)

Ortho-chloro benzyl trifluoro methyl sulphoxide (III) (242.5 gm) and Monochlorobenzene (100 mL) were mixed in 1-lit vertical reactor, followed by the addition of iodine (1 gm) to obtain a mixture. Chlorine gas (71 gm) was then passed through the mixture at 30° C. Since the reaction is exothermic, the first mixture reaches to 50° C. while the chlorine is being passed over a period of 3 hrs to obtain a product mixture. The product mixture comprising ortho-chloro benzyl chloride (IV), monochlorobenzene and trifluoro methyl sulfinyl chloride (I) was distilled upto 95° C. mass temperature and vapor temperature of 40-41° C. to collect trifluoro methyl sulfinyl chloride (144.5 gm).

Yield=94.75%; and
Purity=99.20%.

From the experiments I-IX, it is observed that the temperature condition and addition of solvents can differ on the yield and purity of the final product of the present disclosure. As a low boiling solvent like dichloromethane is having nearly same boiling point of trifluoro methyl sulfinyl chloride and hence it distills together. In some cases, high boiling solvent like monochlorobenzene is not getting distilled with trifluoro methyl sulfinyl chloride.

TECHNICAL ADVANCEMENTS

The present disclosure described herein above has several technical advantages including, but not limited to, the realization of a process for the preparation of Trifluoromethanesulfinyl chloride, that is:

simple;
economical; and
environmental-friendly.

The embodiments herein and the various features and advantageous details thereof are explained with reference to the non-limiting embodiments in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

The foregoing description of the specific embodiments so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the embodiments as described herein.

The use of the expression "at least" or "at least one" suggests the use of one or more elements or ingredients or quantities, as the use may be in the embodiment of the disclosure to achieve one or more of the desired objects or results.

Any discussion of documents, acts, materials, devices, articles or the like that has been included in this specification is solely for the purpose of providing a context for the disclosure. It is not to be taken as an admission that any or all of these matters form a part of the prior art base or were common general knowledge in the field relevant to the disclosure as it existed anywhere before the priority date of this application.

The numerical values mentioned for the various physical parameters, dimensions or quantities are only approximations and it is envisaged that the values higher/lower than the numerical values assigned to the parameters, dimensions or quantities fall within the scope of the disclosure, unless there is a statement in the specification specific to the contrary.

While considerable emphasis has been placed herein on the components and component parts of the preferred embodiments, it will be appreciated that many embodiments can be made and that many changes can be made in the preferred embodiments without departing from the principles of the disclosure. These and other changes in the preferred embodiment as well as other embodiments of the disclosure will be apparent to those skilled in the art from the disclosure herein, whereby it is to be distinctly understood that the foregoing descriptive matter is to be interpreted merely as illustrative of the disclosure and not as a limitation.

The invention claimed is:

1. A process for the preparation of trifluoromethanesulfinyl chloride from ortho-chlorobenzyltrifluoromethylsulfide, said process comprising the following steps:
   (a) mixing ortho-chlorobenzyltrifluoromethylsulfide with at least one fluid medium and water to obtain a first mixture and passing chlorine gas in said first mixture under continuous stirring at a first predetermined temperature to obtain a resultant mixture; wherein said chlorine gas reacts with water to form hypochlorous acid (HOCl) in situ; wherein said first predetermined temperature is in the range of 10° C. to 30° C.; and wherein in the process step (a), the mole ratio of ortho-chlorobenzyltrifluoromethylsulfide and chlorine gas is in the range of 1:1 to 1:1.5;
   (b) allowing said resultant mixture to stand in order to separate an organic phase and an aqueous phase;
   (c) separating said organic phase from said aqueous phase to obtain separated organic phase;
   (d) concentrating said separated organic phase to obtain a second mixture comprising ortho-chlorobenzyltrifluoromethylsulfoxide;
   (e) passing chlorine gas in said second mixture under continuous stirring in the presence of at least one activator at a second predetermined temperature to obtain a product mixture comprising trifluoromethanesulfinyl chloride and ortho-chlorobenzyl chloride; and
   (f) fractionally distilling said product mixture to obtain a first fraction comprising trifluoromethanesulfinyl chloride and a second fraction comprising ortho-chlorobenzyl chloride;
      wherein said chlorine gas in step e) is passed in said second mixture until said second mixture reaches a third predetermined temperature.

2. The process as claimed in claim 1, wherein said second predetermined temperature is in the range of 10° C. to 30° C.

3. The process as claimed in claim 1, wherein said third predetermined temperature is in the range of 10° C. to 90° C.

4. The process as claimed in claim 1, wherein said separated organic phase is washed with an aqueous solution of sodium bi-carbonate and sodium bi-sulfide, prior to step (d).

5. The process as claimed in claim 1, wherein said separated organic phase is concentrated/dehydrated at a temperature in the range of 40° C. to 90° C.

6. The process as claimed in claim 1, wherein said separated organic phase is concentrated by azeotropic distillation till the water content is less than 0.5%.

7. The process as claimed in claim 1, wherein said fluid medium is selected from the group consisting of dichloroethane, dichloromethane, chloroform, monochlorobenzene, bromobenzene, and carbon tetrachloride.

8. The process as claimed in claim 1, wherein the stirring of said first mixture is carried out for a time period in the range of 1 hour to 5 hours and the stirring of said second mixture is carried out for a time period in the range of 1 hour to 5 hours.

9. The process as claimed in claim 1, wherein said activator is selected from the group consisting of iodine, di-tert-butyl peroxide, benzoyl peroxide, and azobisisobutyronitrile.

10. The process as claimed in claim 1, wherein in the process step (e), the mole ratio of ortho-chlorobenzyltrifluoromethylsulfoxide and chlorine gas is in the range of 1:1 to 1:1.5.

11. The process as claimed in claim 1, wherein the mole ratio of ortho-chlorobenzyltrifluoromethylsulfoxide and said activator is in the range of 1:0.001 to 1:0.01.

12. The process as claimed in claim 1, wherein ortho-chlorobenzyl chloride obtained in step (f) is recovered.

13. The process as claimed in claim 1, wherein trifluoromethanesulfinyl chloride has a purity in the range of 95% to 99.9%.

* * * * *